US009770164B2

(12) United States Patent
Sato (10) Patent No.: US 9,770,164 B2
(45) Date of Patent: Sep. 26, 2017

(54) ENDOSCOPE REPROCESSOR (71) Applicant: OLYMPUS CORPORATION, Tokyo (JP)

(72) Inventor: Norito Sato, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 14/934,640

(22) Filed: Nov. 6, 2015

(65) Prior Publication Data
US 2016/0058900 A1 Mar. 3, 2016

Related U.S. Application Data (63) Continuation of application No. PCT/JP2015/061080, filed on Apr. 9, 2015.

(30) Foreign Application Priority Data

Jun. 13, 2014 (JP) ................................. 2014-122674

(51) Int. Cl.
*A61B 1/12* (2006.01)
*A61L 2/18* (2006.01)
*A61B 90/70* (2016.01)

(52) U.S. Cl.
CPC ................ *A61B 1/123* (2013.01); *A61L 2/18* (2013.01); *A61B 2090/701* (2016.02)

(58) Field of Classification Search
CPC ............................................. A61B 1/12–1/125
See application file for complete search history.

(56) References Cited

U.S. PATENT DOCUMENTS

2002/0064479 A1* 5/2002 Nakanishi .......... A61B 1/00059
422/28
2013/0098407 A1* 4/2013 Perlman ................ A61B 1/123
134/36
2014/0134071 A1 5/2014 Suzuki et al.

FOREIGN PATENT DOCUMENTS

| EP | 2803314 A1 | 11/2014 |
| JP | 2009-225811 A | 10/2009 |
| JP | 2009-225813 A | 10/2009 |
| JP | 2010-167284 A | 8/2010 |
| JP | 2011-092425 A | 5/2011 |
| JP | 5572768 B1 | 8/2014 |
| WO | WO 2014/045718 A1 | 3/2014 |

OTHER PUBLICATIONS

Machine Translation JP2009225811 (Oct. 8, 2009).*

* cited by examiner

*Primary Examiner* — Michael Barr
*Assistant Examiner* — Spencer Bell
(74) *Attorney, Agent, or Firm* — Scully, Scott, Murphy & Presser, P.C.

(57) ABSTRACT

An endoscope reprocessor includes an immersion tank, a convex-shaped groove, a lid portion, a liquid supply section, a discharge port as an opening from which the liquid is discharged and which is provided at the liquid supply section, the discharge port being arranged such that a part of the opening is opposed to a side surface of the convex-shaped groove, and a control section that drives the liquid supply section to allow the liquid to be introduced into the immersion tank up to a first water level at which a flat portion of the lid portion is immersed in the liquid, and to allow the liquid to be discharged toward the flat portion and the side surface through the discharge port at the first water level.

5 Claims, 7 Drawing Sheets

ENDOSCOPE REPROCESSOR

CROSS REFERENCE TO RELATED APPLICATION

This application is a continuation application of PCT/JP2015/061080 filed on Apr. 9, 2015 and claims the benefit of Japanese Application No. 2014-122674 filed in Japan on Jun. 13, 2014, the entire contents of which are incorporated herein by this reference.

BACKGROUND OF THE INVENTION

1. Field of the Invention

The present invention relates to an endoscope reprocessor including a liquid supply section that supplies liquid to an immersion tank.

2. Description of the Related Art

In an endoscope reprocessor, an endoscope is cleaned and disinfected by selectively supplying, from a liquid supply section provided in an immersion tank, liquids such as cleaning solution, disinfectant solution, and rinsing water to the immersion tank in which the endoscope is housed, up to a predetermined water level. During a cleaning and disinfecting process, also an inner surface of a lid portion of the endoscope reprocessor which closes the immersion tank is required to be cleaned, disinfected, and rinsed.

Note that the inner surface of the lid portion generally includes a convex-shaped groove in which an upper end side of the liquid supply section is located and a flat portion extending from a lower end of the convex-shaped groove in a horizontal direction, and a configuration is known, in which liquid is supplied from the liquid supplying section to the immersion tank up to the water level at which the flat portion of the lid portion is immersed in the liquid, in order to clean, disinfect, and rinse the flat portion.

When the flat portion of the lid portion is immersed in the liquid, air bubbles sometimes adhere to the flat portion. In such a case, it has been difficult to clean, disinfect, and rinse the part of the flat portion to which air bubbles adhere.

Therefore, in conventional reprocessors, the air bubbles are removed from the flat portion of the lid portion with the flowing liquid, by circulating the liquid, through the use of a liquid circulation port and liquid supply section provided in the immersion tank, back to the immersion tank at the water level at which the flat portion of the lid portion is immersed in the liquid.

Japanese Patent Application Laid-Open Publication No. 2009-225813 discloses a configuration in which a plurality of protrusions and an inclined surface which inclines toward a convex-shaped groove are formed on the flat portion of the lid portion, to move air bubbles from the flat portion toward the convex-shaped groove side with the liquid sent from the liquid supply section by means of a space formed with a plurality of protrusions, the inclined surface, and buoyant force of the air bubbles.

SUMMARY OF THE INVENTION

An endoscope reprocessor according to one aspect of the present invention includes: an immersion tank including a concave portion configured to house an endoscope; a lid portion configured to be able to open and close the immersion tank, the lid portion including, on an inner surface thereof, a convex-shaped groove having a side surface and an upper surface, and a flat portion extending from a lower end of the side surface in a horizontal direction; a liquid supply section that supplies liquid to the immersion tank, the liquid supply section being provided in the immersion tank such that an upper end side is located in the convex-shaped groove; a discharge port as an opening from which the liquid is discharged and which is provided at the liquid supply section, the discharge port being arranged such that a part of the opening is opposed to the side surface; and a control section that drives the liquid supply section to allow the liquid to be introduced into the immersion tank up to a first water level at which the flat portion is immersed in the liquid, and to allow the liquid to be discharged toward the flat portion and the side surface through the discharge port at the first water level.

DETAILED DESCRIPTION OF THE PREFERRED EMBODIMENT

Hereinafter, an embodiment of the present invention will be described with reference to drawings. Note that each of the drawings is a pattern diagram, and care should be taken to the fact that the relationship between the thicknesses and widths of the respective members, a ratio of the thickness of a certain member to that of another member, and the like are different from the actual relationship, ratio, and the like. It is needless to say that the drawings include a part in which a relationship and ratio among the dimensions of the members are different from those in other drawings.

Figure 1:
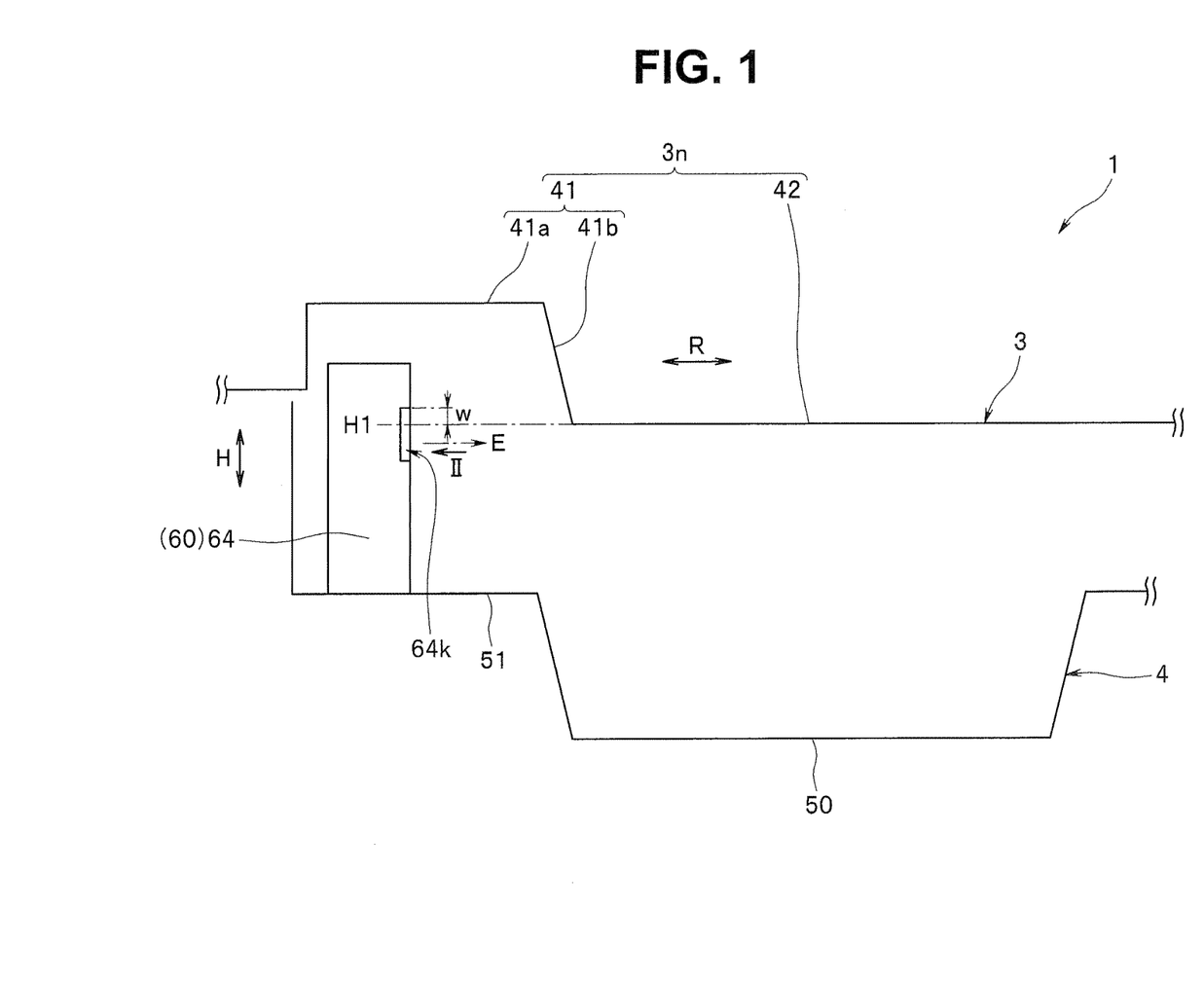
FIG. 1 schematically illustrates a state where a lid portion is closed on an immersion tank in an endoscope reprocessor according to a present embodiment.
Figure 2:
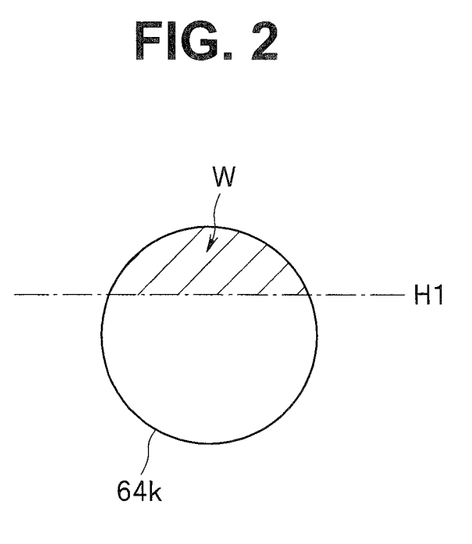
FIG. 2 is a plan view of a discharge port of a liquid supply section in FIG. 1 viewed from the direction II in FIG. 1.

FIG. 1 schematically illustrates a state where a lid portion is closed on an immersion tank in an endoscope reprocessor according to a present embodiment, and FIG. 2 is a plan view of a discharge port of a liquid supply section in FIG. 1 viewed from the direction II in FIG. 1.

The endoscope reprocessor according to the present invention is an apparatus for performing reprocessing on a contaminated endoscope and endoscope accessories.

The reprocessing in the present invention is not particularly limited, but includes rinsing with water, cleaning for removing dirt such as organic substances, disinfection for making specific microorganisms ineffectual, and sterilization for expelling or killing all microorganisms, or any combination of these.

As shown in FIG. 1, an endoscope reprocessor 1 includes an immersion tank 4 in which an endoscope 100 (see FIG. 3) is housed, and a lid portion 3 configured to be able to open and close the immersion tank 4.

The lid portion 3 includes: on an inner surface 3n thereof, recess 41 including a circumferential side surface 41h extending along a height direction H and a bottom surface 41a that covers an upper end in the height direction H of the side surface 41b; and a flat portion 42 extending in a horizontal direction R from a periphery of the lower end in the height direction H of the side surface 41b.

The flat portion 42 is immersed in a liquid E when the liquid E is introduced into the immersion tank 4 up to a first water level H1.

In addition, the recess 41 is located at a position higher than the position of the flat portion 42 in the height direction H, which prevents the bottom surface 41a and the side surface 41b of the recess 41 from being immersed in the liquid E when the liquid E is introduced into the immersion tank 4 up to the first water level H1. Note that the liquid E includes cleaning solution, disinfectant solution, or rinsing water, etc.

The immersion tank 4 includes a concave portion 50 in which an endoscope 100 is housed, and a terrace portion 51 formed so as to be continuous with an outer peripheral edge of the upper end in the height direction H of the concave portion 50. At the terrace portion 51, a liquid supply nozzle 64 of a liquid supply section 60 that supplies the liquid E to the immersion tank 4 is disposed. When the lid portion 3 is closed on the immersion tank 4, the upper end side of the liquid supply nozzle 64 is located in the recess 41.

In addition, the liquid supply nozzle 64 includes a discharge port 64k as an opening from which the liquid E is discharged. The discharge port 64k is arranged so as to be opposed to the flat portion 42 of the lid portion 3 closed on the immersion tank 4, and as shown in FIGS. 1 and 2, a predetermined proportion W of the opening area of the discharge port 64k is opposed to the side surface 41b of the convex-shaped groove 41.

The liquid supply nozzle 64 supplies the liquid E to the immersion tank 4 up to the first water level H1 through the discharge port 64k, and discharges the liquid E toward the flat portion 42 and the side surface 41b at the first water level H1.

Figure 8:
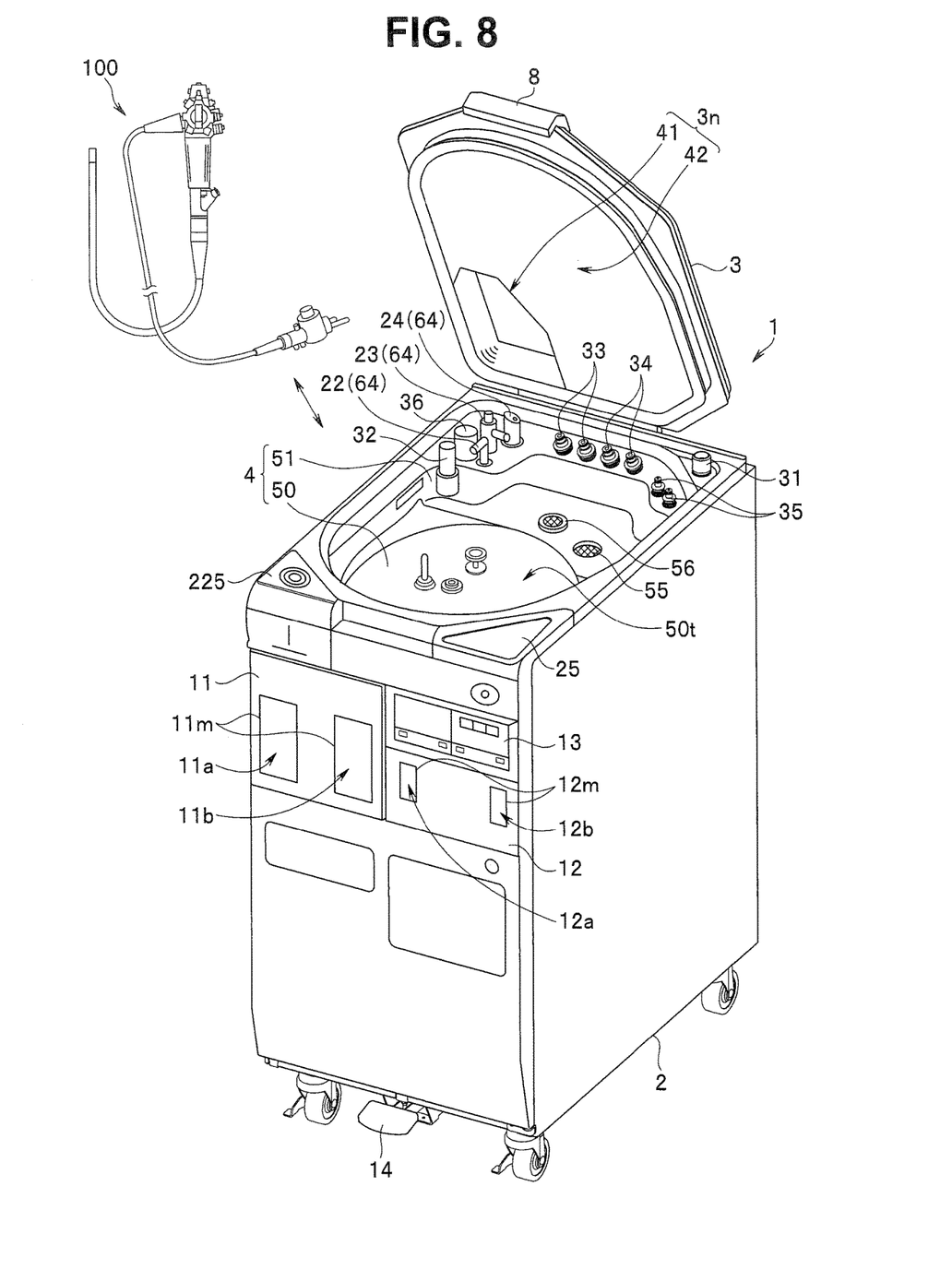
FIG. 8 is a perspective view of one example of the endoscope reprocessor in a state where the lid portion is open and an endoscope can be housed in the immersion tank.

Furthermore, the terrace portion 51 includes, other than the liquid supply nozzle 64, also a water level detection portion 32 that detects the first water level H1 of the liquid E supplied to the immersion tank 4 and a water level detection portion 36 that detects a second water level H2 (see FIG. 3) higher than the first water level H1, to prevent the liquid E from overflowing from the immersion tank 4, as shown in FIG. 8 to be described later. Note that the water level detection portion 32 and the water level detection portion 36 may be formed integrally.

Furthermore, the first water level H1 to be detected by the water level detection portion 32 is set to be slightly higher than the flat portion 42 in the height direction H in the state where the lid portion 3 is closed on the immersion tank 4. The first water level H1 is thus set so as to surely allow the flat portion 42 to be immersed in the liquid E, when the liquid E is introduced into the immersion tank 4 up to the first water lever H1.

Furthermore, when the second water level H2 is detected by the water level detection portion 36, if the liquid E is continued to be supplied into the immersion tank 4, the liquid E overflows from the immersion tank 4. Therefore, control for stopping the driving of various pumps for supplying the liquid E to the immersion tank 4 is performed by the control section 70 to be described later.

In addition, as shown in FIG. 8 to be described later, the liquid supply nozzle 64 includes a water-supply circulation nozzle 24 that causes the liquid E to circulate into the immersion tank 4, a cleaning solution nozzle 22 disposed at the liquid supply section 60 and configured to supply cleaning solution to the immersion tank 4, a disinfectant solution nozzle 23 disposed at the liquid supply section 60 and configured to supply disinfectant solution to the immersion tank 4, and the like.

Figure 3:
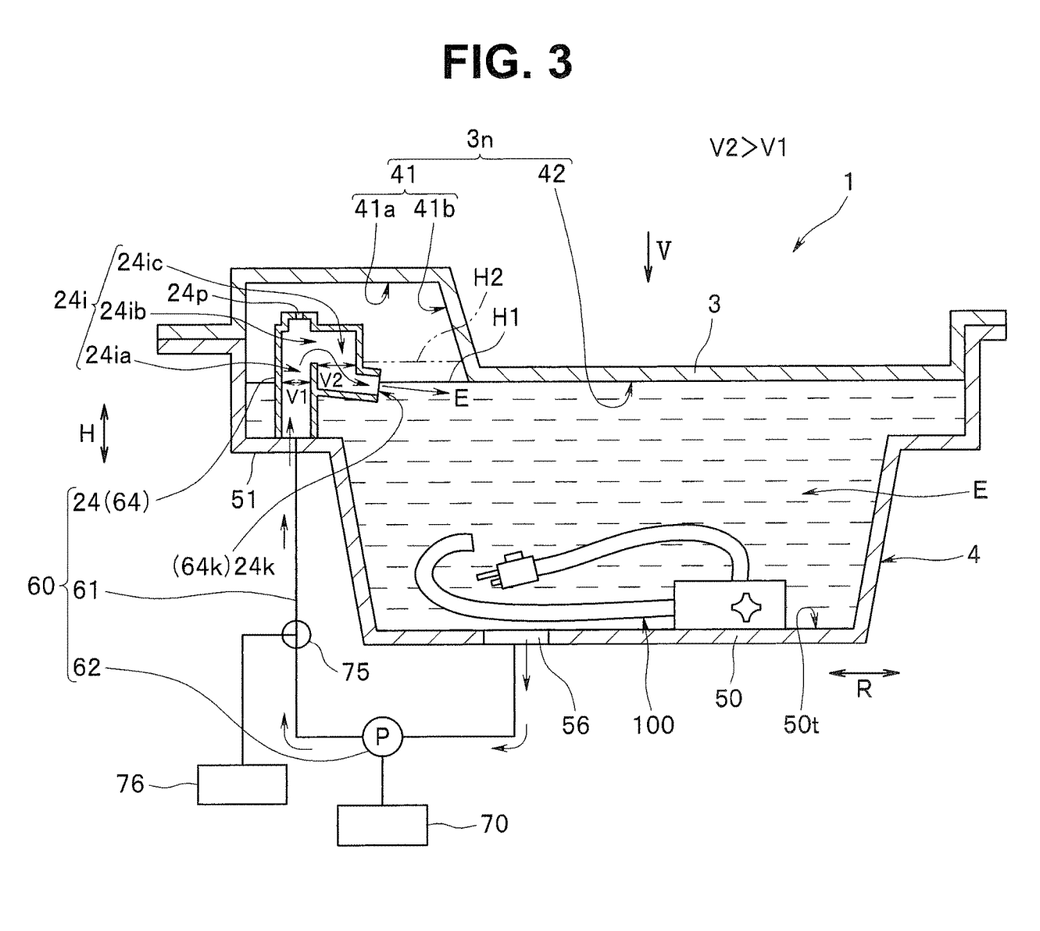
FIG. 3 is a partial cross-sectional view schematically illustrating a configuration for supplying, to the immersion tank, liquid from the discharge port of a water-supply circulation nozzle provided in the endoscope reprocessor in FIG. 1 in the state where the lid portion is closed on the immersion tank.

Next, with reference to FIG. 3, description will be schematically made on the configuration in which the liquid E is supplied from the discharge port of the liquid supply nozzle into the immersion tank 4 in FIG. 1, by taking the water-supply circulation nozzle as an example.

FIG. 3 is a partial cross-sectional view schematically illustrating a configuration for supplying the liquid, to the immersion tank, from the discharge port of a water-supply circulation nozzle provided in the endoscope reprocessor in FIG. 1 in the state where the lid portion is closed on the immersion tank.

As shown in FIG. 3, a circulation port 56 is provided in the immersion tank 4 at a position lower than the position of the water level detection portion 32, for example, at the position on the bottom surface 50t of the concave portion 50. Note that the position of the circulation port 56 is not limited to the position on the bottom surface 50t.

In addition, the endoscope reprocessor 1 includes the liquid supply section 60 including the water-supply circulation nozzle 24, a water-supply circulation conduit 61, and a circulation pump 62.

One end of the water-supply circulation conduit 61 is connected to a nozzle conduit 24i provided in the water-supply circulation nozzle 24, and the other end of the water-supply circulation conduit 61 is connected to the circulation port 56. In addition, a three-way valve 75 is interposed at the halfway position of the water-supply circulation conduit 61, and the three-way valve 75 is connected with a water tap 76.

Note that the configuration of the water-supply circulation nozzle 24 is the same as that of the above-described liquid supply nozzle 64. That is, when the lid portion 3 is closed on the immersion tank 4, the upper end side of the water-supply circulation nozzle 24 is located in the recess 41.

In addition, the water-supply circulation nozzle 24 includes a discharge port 24k as an opening from which the liquid E is discharged. The discharge port 24k is arranged so as to be opposed to the flat portion 42 of the lid portion 3 closed on the immersion tank 4, and similarly as the discharge port 64k, a predetermined proportion W of the opening area of the discharge port 24k is opposed to the side surface 41b of the recess 41.

The water-supply circulation nozzle 24 supplies water coming from the water tap 76 to the immersion tank 4 through the discharge port 24k via the water-supply circulation conduit 61 and the nozzle conduit 24i, and causes the liquid E in the immersion tank 4 to be passed through the circulation port 56, the water-supply circulation conduit 61, and the nozzle conduit 24i, and then supplied again from the discharge port 24k to the immersion tank 4. Thus, the liquid E is circulated back to the immersion tank 4.

The circulation pump 62 is interposed in the water-supply circulation conduit 61 so as to be located at the halfway position which is close to the circulation port 56 with respect to the three-way valve 75. The circulation pump 62 is controlled to be driven by the control section 70 in the endoscope reprocessor 1.

Note that the control section 70 controls to drive also pumps, not shown, respectively interposed in conduits, not shown, each of which is connected to the cleaning solution nozzle 22 or the disinfectant solution nozzle 23 such that cleaning solution or disinfectant solution is supplied to the immersion tank 4 from the cleaning solution nozzle 22 or the disinfectant solution nozzle 23, these nozzles constituting the liquid supply section 60.

For example, the control section 70 drives the pump interposed in the conduit of the disinfectant solution nozzle 23, to thereby introduce the disinfectant solution from the disinfectant solution nozzle 23 into the immersion tank 4 up to the first water level H1, and drives the circulation pump 62, to thereby cause the disinfectant solution in the immersion tank 4 to pass through the circulation port 56, the water-supply circulation conduit 61, and the nozzle conduit 24i of the water-supply circulation nozzle 24, and to be discharged from the discharge port 24k toward the flat portion 42 and the side surface 41b at the first water level H1.

The nozzle conduit 24i includes a first part 24ia, a second part 24ic, and a turn-back portion 24ib.

The first part 24ia is a part extending from the lower side toward the upper side in the height direction H in the nozzle conduit 24i.

The second part 24ic is a part which communicates with the discharge port 24k and which extends from the upper side toward the lower side in the height direction H in the nozzle conduit 24i.

The turn-back portion 24ib is connected with the first part 24ia and the second part 24ic at the position higher than the second water level H2 in the height direction H, and turns back the extending direction of the nozzle 24i from the first part 24ia toward the second part 24ic.

The discharge port 24k is located so as to communicate with the second part 24ic, that is, disposed at the position lower than the turn-back portion 24ib in the height direction H.

Note that, as described above, the discharge port 24k is opposed to the flat portion 42 of the lid portion 3 closed on the immersion tank 4, and arranged such that the predetermined proportion W of the opening area of the discharge port 24k is opposed to the side surface 41b of the recess 41.

However, even if the liquid E is introduced into the immersion tank 4 up to the first water level H1 at which the flat portion 42 is immersed in the liquid E or up to the second water level H2 higher than the first water level H1, the turn-back portion 24ib located at the position higher than the second water level H2 prevents the liquid E from flowing back toward the water-supply circulation conduit 61 in the nozzle conduit 24i.

The object of this configuration is to prevent the dirt in the immersion tank 4 from entering the water-supply circulation conduit 61 together with the liquid E, and also to prevent the liquid E in the immersion tank 4 from flowing back to the water tap 76, since the water-supply circulation conduit 61 is connected also with the water tap 76, as described above.

In addition, the cross-sectional area V2 of the second part 24ic is larger than the cross-sectional area V1 of the first part 24ia (V2>V1).

If the cross-sectional area of the second part 24ic is equal to or smaller than the cross-sectional area of the first part 24ia, the flow rate of the liquid E flowing through the second part 24ic toward the discharge port 24k becomes lower than the flow rate of the liquid E flowing through the first part 24ia due to the conduit resistance at the turn-back portion 24ib.

That is, the above-described configuration is for preventing the decrease of the flow rate of the liquid E to be discharged from the discharge port 24k, and sufficiently ensuring the flow rate of the liquid E supplied from the discharge port 24k to the side surface 41b and the flat portion 42.

Furthermore, another opening portion 24p which communicates with the nozzle conduit 24i is arranged at the upper end of the water-supply circulation nozzle 24, the upper end being opposed to the bottom surface 41a of the recess 41.

The liquid E flowing through the nozzle conduit 24i is discharged from the other opening portion 24p toward the bottom surface 41a, which allows the upper surface 41a and the side surface 41b to be cleaned, disinfected, and rinsed, and prevents backward flow of the liquid E toward the water-supply circulation conduit 61 by some sort of negative pressure generated in the nozzle conduit 24i.

Figure 4:
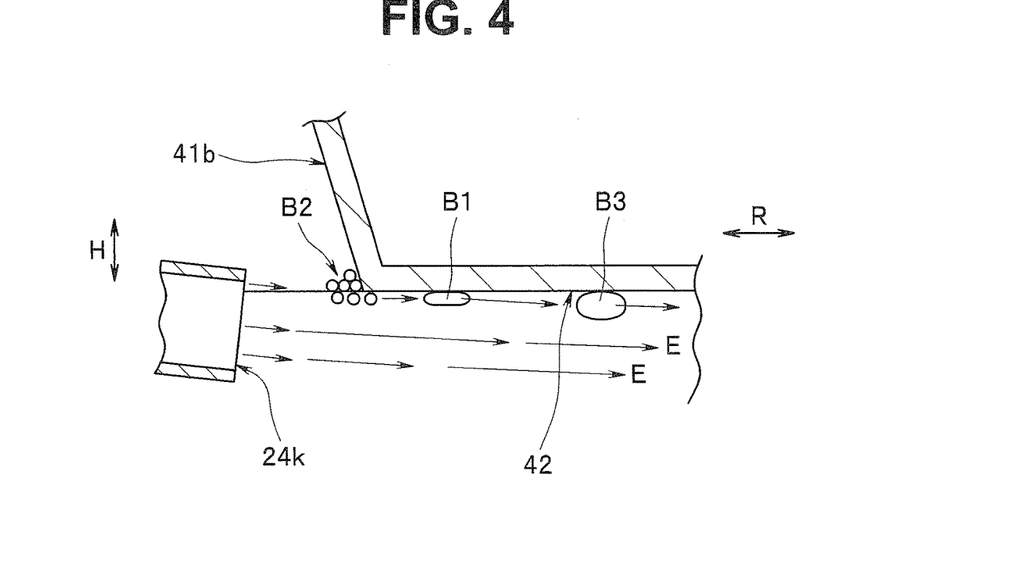
FIG. 4 is a partial cross-sectional view schematically illustrating a state where the liquid is sent from the discharge port of the water-supply circulation nozzle in FIG. 3 to a flat portion and a side surface of the lid portion.

Next, the working of the present embodiment will be briefly described with reference to FIG. 4. FIG. 4 is a partial cross-sectional view schematically illustrating the state where liquid is sent from the discharge port of the water-supply circulation nozzle in FIG. 3 to the flat portion and the side surface of the lid portion. Note that, hereinafter description will be made by taking the case where the flat portion 42 of the lid portion 3 is disinfected together with the endoscope 100 as an example.

When the endoscope 100 housed in the immersion tank 4 is disinfected, the control section 70 first drives the pump connected to the conduit of the disinfectant solution nozzle 23, to allow the disinfectant solution to be supplied from the disinfectant solution nozzle 23 to the immersion tank 4. At this time, in order to disinfect also the flat portion 42 of the lid portion 3, the disinfectant solution is supplied up to the first water level H1 at which the flat portion 42 is immersed in the disinfectant solution.

As a result, the flat portion 42 is immersed in the disinfectant solution. However, as shown in FIG. 4, there is a case where air bubbles B1 adhere to the flat portion 42.

In order to remove the air bubbles B1 from the flat portion 42, the circulation pump 62 is driven by the driving control performed by the control section 70, to thereby cause the disinfectant solution in the immersion tank 4 to pass through the circulation port 56, the water-supply circulation conduit 61, and the nozzle conduit 24i and then to be discharged from the discharge port 24k to the immersion tank 4.

In the present embodiment, the discharge port 24k is arranged so as to be opposed to the flat portion 42 of the lid portion 3 closed on the immersion tank 4, and the predetermined proportion W of the opening area of the discharge port 24k is opposed to the side surface 41b of the recess 41. Therefore, the disinfectant solution discharged from the discharge port 24k is directly sent to the flat portion 42 which is opposed to the discharge port 24k, and also sent to the side surface 41b.

Furthermore, as described above, the cross-sectional area V2 of the second part 24ic is larger than the cross-sectional area V1 of the first part 24ia, which allows the sufficient flow rate of disinfectant solution to be supplied to the flat portion 42 and the side surface 41b.

The disinfectant solution sent to the side surface 41b collides with the side surface 41b, which generates air bubbles B2 on the surface of the disinfectant solution retained in the immersion tank 4 up to the first water level H1. The air bubbles B2 are mixed in the sending of the disinfectant solution supplied from the discharge port 24k to the flat portion 42, to collide with the air bubbles B1 adhered to the flat portion.

As a result, the air bubble B2 become large air bubbles B3, while engulfing the air bubbles B1, and the resultant air bubbles B3 are likely to be separated from the flat portion 42 with the supply of the disinfectant solution from the discharge port 24k toward the flat portion 42. That is, the air bubbles can be easily removed.

Thus, in the present embodiment, the air bubbles B1 adhered to the flat portion 42 are removed not only by sending the liquid E but also by using the air bubbles B2 generated with the sending of the liquid to the side surface 41b.

Note that the above-described working is not limited to the disinfectant solution but is the same also regarding the cleaning solution, rinsing water, or the like. In addition, the working is not limited to the water-supply circulation nozzle 24 but is the same in the case where another nozzle such as the liquid supply nozzle 64 is used.

Thus, in the present embodiment, the discharge port 64k of the liquid supply nozzle 64 is opposed to the flat portion 42 of the lid portion 3 closed on the immersion tank 4, and disposed such that the predetermined proportion W of the opening area of the discharge port 64k is opposed to the side surface 41b of the recess 41.

According to this configuration, even if the air bubbles B1 adhere to the flat portion 42 when the liquid E is introduced into the immersion tank 4 up to the first water level H1 and the flat portion 42 is immersed in the liquid E, the discharge port 64k is arranged so as to be opposed to the flat portion 42 and a part of the discharge port 64k is located at substantially the same height as the flat portion 42, which enables the liquid E to be directly supplied toward the flat portion 42 at the optimal angle.

In addition, since the predetermined proportion W of the discharge port 64k is opposed to the side surface 41b, the liquid E discharged from the discharge port 64k is caused to collide with the side surface 41b to generate the air bubbles B2 on the surface of the liquid E, and the generated air bubbles B2, together with the liquid E, are caused to collide with the air bubbles B1, which enables the large air bubbles B3 to be formed.

According to the above-described configuration, the air bubbles adhered to the flat portion 42 by the liquid E supplied from the discharge port 64k to the flat portion 42 are enlarged with the collision of the air bubbles B2, to become the air bubbles B3 which are likely to be separated from the flat portion 42. Such air bubbles B3 can be easily removed by sending the liquid from the discharge port 64k.

In addition, even if a part of the discharge port 64k is located at the position lower than the first water level H1, the nozzle conduit 24i includes the turn-back portion 24ib located at the position higher than the second water level H2, which prevents the liquid E in the immersion tank 4 from flowing back in the nozzle conduit 24i through the discharge port 64k.

As described above, the present invention is capable of providing the endoscope reprocessor 1 configured to be able to easily remove the air bubbles B1 adhered to the flat portion 42 of the lid portion 3 with the liquid sent from the liquid supply section 60.

In the present embodiment, description has been made by taking the liquid supply section 60 including the water-supply circulation nozzle 24, the water-supply circulation conduit 61, and the circulation pump 62 as an example. However, the liquid supply section 60 is not limited to such a configuration.

The liquid supply section 60 has only to have a structure for supplying liquid to the immersion tank 4, and may be configured by the water-supply circulation nozzle 24, the water-supply circulation conduit 61, and an adjusting section that adjusts the inner pressure of the immersion tank 4, for example.

Figure 5:
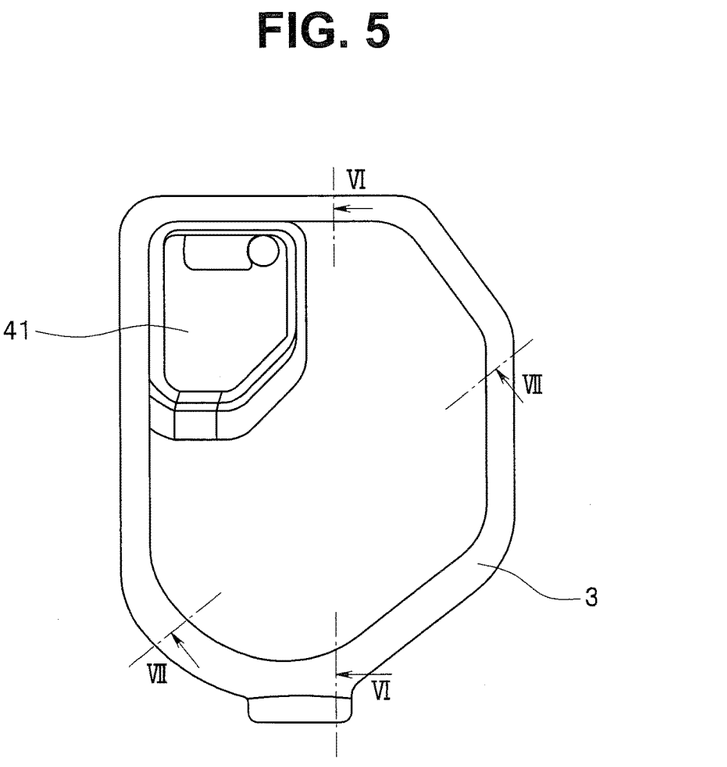
FIG. 5 is a top view of the lid portion in FIG. 3 viewed from the direction V in FIG. 3.

Note that, hereinafter, a modified example will be described with reference to FIGS. 5 to 7. FIG. 5 is a top view of the lid portion in FIG. 3 viewed from the direction V in FIG. 3, FIG. 6 is a cross-sectional view of the lid portion taken along the VI-VI line in FIG. 5, and FIG. 7 is a cross-sectional view of the lid portion taken along the VII-VII line in FIG. 5.

Figure 6:
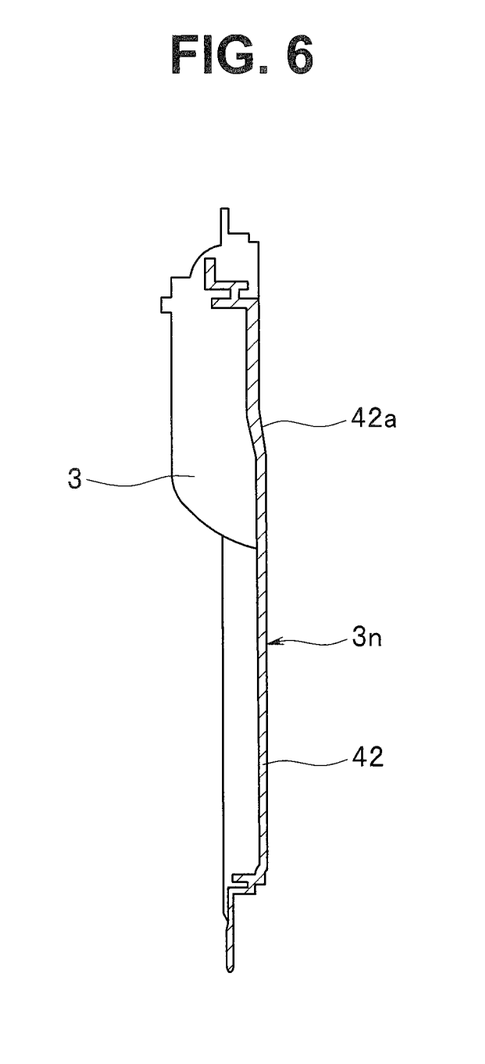
FIG. 6 is a cross-sectional view of the lid portion taken along the VI-VI line in FIG. 5.
Figure 7:
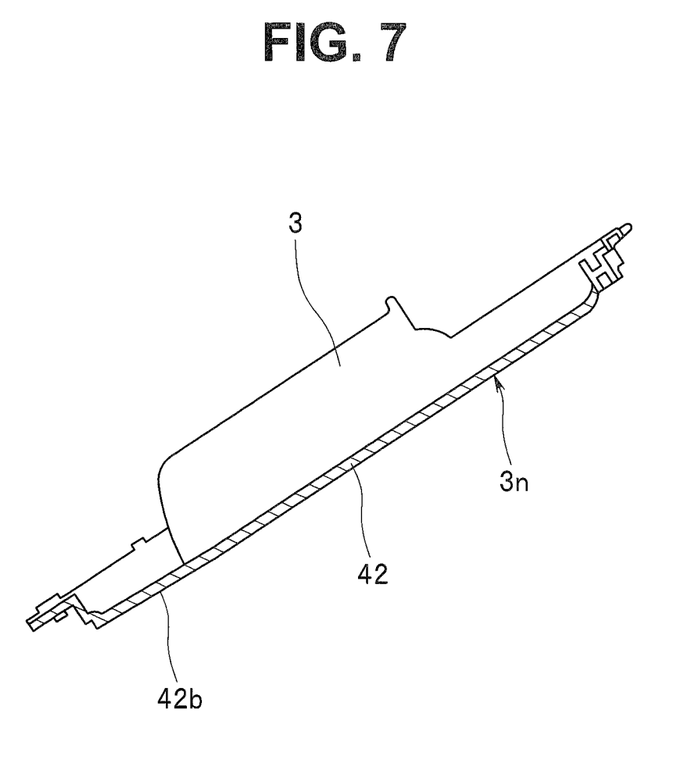
FIG. 7 is a cross-sectional view of the lid portion taken along the VII-VII line in FIG. 5.

As shown in FIGS. 5 to 7, the flat portion 42 on an inner surface 3n of the lid portion 3 may include inclined surfaces 42a, 42b inclined so as to become higher from substantially the center portion of the inner surface 3n respectively toward the recess 41 and the outer periphery of the lid portion 3.

According to such a configuration, with sending of the liquid from the discharge port 64k to the flat portion 42, the air bubbles B1 adhered to substantially the center portion of the flat portion 42 can be easily moved toward the recess 41 and the outer peripheral side of the lid portion 3 through the use of the inclined surfaces 42a, 42b.

Note that it is needless to say that the positions of the inclined surfaces on the flat portion 42 are not limited to those shown in FIGS. 6 and 7, and various positions can be assumed so as to allow the air bubbles B1 to be moved easily.

Next, one example of the endoscope reprocessor 1 according to the present embodiment will be described with reference to FIG. 8. FIG. 8 is a perspective view of one example of the endoscope reprocessor in the state where the lid portion is open and the endoscope can be housed in the immersion tank.

As shown in FIG. 8, the endoscope reprocessor 1 is an apparatus for washing and disinfecting the endoscope 100 after use, and includes a main part configured by the apparatus main body 2, and the lid portion 3 connected to the upper part of the apparatus main body 2 so as to be openable/closable with a hinge, not shown, for example.

When the lid portion 3 is closed on the apparatus main body 2, the apparatus main body 2 and the lid portion 3 are fixed, for example, with a latch 8 disposed at the opposed positions of the apparatus main body 2 and the lid portion 3.

A cleaning solution/alcohol tray 11 is disposed at the upper part of a left half portion, for example, on the front face in FIG. 8, of the apparatus main body 2 so as to be drawable forward of the apparatus main body 2, the front face being a side toward which the operator approaches.

The cleaning solution/alcohol tray 11 houses a cleaning solution tank 11a in which the cleaning solution used for cleaning the endoscope 100 is retained, and an alcohol tank 11b in which alcohol used for drying the endoscope 100 subjected to the reprocessing is retained, and the liquids can be appropriately filled in the tanks 11a, 11b since the cleaning solution/alcohol tray 11 is drawable.

Note that the cleaning solution/alcohol tray 11 is provided with two window portions 11m through which the operator can confirm the remaining amounts of the cleaning solution and alcohol filled respectively in the tanks 11a, 11b.

In addition, a disinfectant solution tray 12 is disposed at the upper part of a right half portion, for example, on the front face of the apparatus main body 2 so as to be drawable forward of the apparatus main body 2.

The disinfectant solution tray 12 houses two medicinal solution bottles 12a, 12b into which a disinfectant solution such as peracetic acid to be used for disinfecting the endoscope 100 is injected. The disinfectant solution tray 12 is drawable, which enables the two medicinal solution bottles 12a, 12b to be appropriately set.

Note that the disinfectant solution tray 12 includes two window portions 12m through which the operator can confirm the remaining amounts of the disinfectant solutions filled in the respective medicinal solution bottles 12a, 12b.

Furthermore, a sub operation panel 13, which includes instruction buttons for displaying cleaning/disinfecting time and warming the disinfectant solution, is disposed above the disinfectant solution tray 12 on the front face of the apparatus main body 2.

Furthermore, a pedal switch 14 is disposed at the lower part on the front face in FIG. 8 of the apparatus main body 2, the pedal switch being configured to open upward the lid portion 3 closed on the upper part of the apparatus main body 2 by stepping-on operation by the operator.

In addition, the apparatus main body 2 includes, for example, on the upper surface thereof, a main operation panel 25 at the position close to the right end on the front face side where the operator approaches, the main operation panel including setting switches such as a switch for starting cleaning and disinfecting operation of the apparatus main body 2 and a cleaning/disinfecting mode selection switch, and a receiving portion 22S at the position close to the left end on the front face side where the operator approaches, the receiving portion being configured by RFID (radio frequency identifier) that receives information from the endoscope 100 when the endoscope is brought close thereto.

In addition, a water supply hose connecting port 31 is disposed on the upper surface of the apparatus main body 2 so as to be located on a rear face side opposing to the front face toward which the operator approaches, the water supply hose connecting port 31 being connected with a water supply hose, not shown, which is connected to the water tap 76 (see FIG. 3) for supplying tap water to the apparatus main body 2. Note that the water supply hose connecting port 31 may be provided with a mesh filter for filtering the tap water.

Furthermore, the immersion tank 4, which can house the endoscope 100 and has an endoscope housing opening configured to be opened and closed by the lid portion 3, is disposed at a substantially center portion of the upper surface of the apparatus main body 2.

The immersion tank 4 includes the concave portion 50 in which the endoscope 100 is housed and the terrace portion 51 provided peripherally so as to be continuous with the outer peripheral edge of the concave portion 50, as described above.

The concave portion 50 includes, on the bottom surface 50t, a drainage port 55 for draining from the immersion tank 4 the cleaning solution, water, alcohol, disinfectant solution or the like supplied to the immersion tank 4, and the circulation port 56 for supplying the cleaning solution, water, disinfectant solution or the like supplied to the immersion tank 4 to the respective conduits provided inside the endoscope 100 or for resupplying the above-described liquid from the water-supply circulation nozzle 24 to the immersion tank 4 through the mesh filter and the like. Note that the circulation port 56 may be provided with a mesh filter for filtering the cleaning solution and the like.

The terrace portion 51 includes, at arbitrary positions thereof, the water level detection portion 32 with a cover, which is configured to detect the first water level H1 of the cleaning solution, water, disinfectant solution, etc., supplied to the immersion tank 4 and the water level detection portion 36 configured to detect the second water level H2.

In addition, the terrace portion 51 includes the cleaning solution nozzle 22 for supplying the cleaning solution to be diluted with tap water to a predetermined concentration from the cleaning solution tank 11a to the immersion tank 4 and the disinfectant solution nozzle 23 for supplying the disinfectant solution to the immersion tank 4.

The terrace portion 51 further includes the water-supply circulation nozzle 24 for supplying water to the immersion tank 4 or resupplying the cleaning solution, water, disinfectant solution and the like, which are sucked through the circulation port 56, to the immersion tank 4.

Furthermore, the terrace portion 51 includes a plurality of, for example, two air and water feeding/forceps port connectors 33 for supplying cleaning solution, water, alcohol, disinfectant solution, or air etc., to the air/water feeding conduit and the suction conduit provided inside the endoscope 100, a plurality of, for example, two auxiliary water feeding/forceps raising connectors 34 for supplying cleaning solution, water, alcohol, disinfectant solution, or air etc., to the auxiliary water feeding conduits provided inside the endoscope 100, and a water leakage detection connector 35 that detects water leakage of the endoscope 100.

Note that it is needless to say that the above-described configuration of the endoscope reprocessor is just one example, and the endoscope reprocessor is not limited to the configuration.

What is claimed is:

1. An endoscope reprocessor comprising:
    an immersion tank including a concave portion configured to house an endoscope;
    a lid portion configured to be able to open and close the immersion tank, the lid portion including, on an inner surface thereof, a recess having a side surface and a bottom surface, and a flat portion extending from a lower end of the side surface in a horizontal direction;
    a liquid supply section that supplies liquid to the immersion tank, the liquid supply section being provided in the immersion tank such that an upper end side is located in the recess;
    a discharge port as an opening from which the liquid is discharged and which is provided at the liquid supply section, the discharge port being oriented such that the liquid is discharged partially at the side surface and partially at a transition from the side surface to the flat portion; and
    a controller configured to drive the liquid supply section to:
       allow the liquid to be introduced into the immersion tank up to a first liquid level at which the flat portion is immersed in the liquid, wherein the first liquid level is within the opening of the discharge port such that the opening is partially submerged in the liquid, and
       allow the liquid to be discharged toward the flat portion and the side surface through the discharge port at the first liquid level.

2. The endoscope reprocessor according to claim 1, further comprising
    a liquid level detection portion that detects the first liquid level and a second liquid level higher than the first liquid level,
    wherein the liquid supply section includes a conduit which communicates with the discharge port, the conduit includes a turn-back portion at a position higher than the second liquid level, the turn-back portion being configured to turn an extending direction of the conduit, which extends from a lower side to an upper side in a direction opposite to a direction of gravitational force, back from the upper side to the lower side in the direction of gravitational force, and the discharge port is arranged at a position lower than the second liquid level.

3. The endoscope reprocessor according to claim 1, wherein the discharge port is arranged such that a predetermined proportion of an area of the opening is opposed to the side surface, which causes air bubbles to be generated on a surface of the liquid due to collision of the liquid against the side surface when the liquid is discharged in a state where the liquid is introduced up to the first liquid level, and the air bubbles generated on the surface of the liquid are supplied to the flat portion together with a flow of the liquid, to thereby remove air bubbles adhered to the flat portion.

4. The endoscope reprocessor according to claim 1, wherein the liquid supply section includes a water-supply circulation nozzle that supplies water from a water tap to the immersion tank and supplies the liquid, which has been circulated, to the immersion tank.

5. The endoscope reprocessor according to claim 1, wherein an other opening is arranged on an upper end of the liquid supply section, the other opening discharging the liquid to the bottom surface of the recess.

\* \* \* \* \*